(12) United States Patent
Pai et al.

(10) Patent No.: US 9,107,645 B2
(45) Date of Patent: *Aug. 18, 2015

(54) APPARATUS AND METHODS FOR SEALING A PUNCTURE IN TISSUE

(75) Inventors: Suresh S. Pai, Mountain View, CA (US); Celso J. Bagaoisan, Union City, CA (US); Juan Domingo, Union City, CA (US)

(73) Assignee: Access Closure, Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/210,363

(22) Filed: Aug. 15, 2011

(65) Prior Publication Data

US 2011/0301640 A1 Dec. 8, 2011

Related U.S. Application Data

(63) Continuation of application No. 11/112,877, filed on Apr. 22, 2005, now Pat. No. 8,002,742.

(51) Int. Cl.
*A61B 17/00* (2006.01)
*A61M 25/10* (2013.01)

(52) U.S. Cl.
CPC ..... *A61B 17/0057* (2013.01); *A61B 2017/0065* (2013.01); *A61B 2017/00637* (2013.01); *A61M 25/10181* (2013.11); *A61M 25/10182* (2013.11); *A61M 2025/1068* (2013.01)

(58) Field of Classification Search
CPC ............ A61M 25/10; A61M 25/1018; A61M 25/10181; A61M 25/10182; A61M 25/10183
USPC ............... 604/96.01, 97.01–97.03, 98.01; 606/191–194

See application file for complete search history.

(56) References Cited

U.S. PATENT DOCUMENTS

| | | | |
|---|---|---|---|
| 2,632,445 A | 3/1953 | Kas, Sr. | |
| 3,799,172 A | 3/1974 | Szpur | |
| 3,923,065 A | 12/1975 | Nozick et al. | |
| 4,271,839 A | 6/1981 | Fogarty et al. | |
| 4,598,707 A | 7/1986 | Agdanowski et al. | |
| 4,738,658 A | 4/1988 | Magro | |
| 4,743,230 A * | 5/1988 | Nordquest | 604/97.02 |
| 4,813,934 A | 3/1989 | Engelson et al. | |
| 4,948,092 A | 8/1990 | Kasper et al. | |
| 5,085,249 A | 2/1992 | Dragan et al. | |
| 5,087,246 A | 2/1992 | Smith | |
| 5,108,421 A | 4/1992 | Fowler | |

(Continued)

FOREIGN PATENT DOCUMENTS

| | | |
|---|---|---|
| EP | 0476178 | 3/1992 |
| EP | 0482350 | 4/1992 |

(Continued)

*Primary Examiner* — Nathan R Price
(74) *Attorney, Agent, or Firm* — Nada J. Ardeleanu

(57) ABSTRACT

An occlusion device for sealing a puncture through tissue includes a tubular wire member having a proximal end, a distal end sized for insertion into the puncture, a lumen extending between the proximal and distal ends, a port adjacent the proximal end communicating with the lumen, and a balloon on the distal end. A source of fluid is connectable to the wire member for delivering fluid via the port into the lumen for expanding the balloon. A piston is movable axially within the wire member to allow fluid to be delivered into the lumen, to isolate the lumen, and to deliver fluid within the lumen into the balloon to expand the balloon.

24 Claims, 11 Drawing Sheets

(56) References Cited

U.S. PATENT DOCUMENTS

| | | |
|---|---|---|
| 5,192,302 A | 3/1993 | Kensey et al. |
| 5,221,259 A | 6/1993 | Weldon |
| 5,222,974 A | 6/1993 | Kensey et al. |
| 5,290,310 A | 3/1994 | Makower |
| 5,292,332 A | 3/1994 | Lee |
| 5,324,306 A | 6/1994 | Makower |
| 5,334,216 A | 8/1994 | Vidal |
| 5,370,660 A | 12/1994 | Weinstein |
| 5,383,896 A | 1/1995 | Gershony |
| 5,413,571 A | 5/1995 | Katsaros |
| 5,419,765 A | 5/1995 | Weldon |
| 5,431,639 A | 7/1995 | Shaw |
| 5,437,292 A | 8/1995 | Kipshidze |
| 5,437,631 A | 8/1995 | Janzen |
| 5,464,396 A | 11/1995 | Barta |
| 5,486,195 A | 1/1996 | Myers |
| 5,507,727 A | 4/1996 | Crainich |
| 5,514,158 A | 5/1996 | Kanesaka |
| 5,529,577 A | 6/1996 | Hammerslag |
| 5,550,187 A | 8/1996 | Rhee |
| 5,571,181 A | 11/1996 | Li |
| 5,580,923 A | 12/1996 | Yeung |
| 5,626,601 A | 5/1997 | Gershony |
| 5,643,464 A | 7/1997 | Rhee |
| 5,716,375 A | 2/1998 | Fowler |
| 5,725,498 A | 3/1998 | Janzen |
| 5,725,551 A | 3/1998 | Myers |
| 5,744,153 A | 4/1998 | Yewey |
| 5,752,974 A | 5/1998 | Rhee |
| 5,780,044 A | 7/1998 | Yewey |
| 5,782,860 A | 7/1998 | Epstein |
| 5,785,679 A | 7/1998 | Abolfathi |
| 5,868,778 A | 2/1999 | Gershony |
| 5,928,266 A | 7/1999 | Kontos |
| 5,951,583 A | 9/1999 | Jensen |
| 5,957,952 A | 9/1999 | Gershony |
| 6,017,359 A | 1/2000 | Gershony |
| 6,022,361 A | 2/2000 | Epstein |
| 6,027,471 A | 2/2000 | Fallon |
| 6,048,358 A | 4/2000 | Barak |
| 6,051,248 A | 4/2000 | Sawhney |
| 6,056,768 A | 5/2000 | Cates |
| 6,083,522 A | 7/2000 | Chu |
| 6,152,943 A | 11/2000 | Sawhney |
| 6,162,240 A | 12/2000 | Cates |
| 6,162,241 A | 12/2000 | Coury |
| 6,165,201 A | 12/2000 | Sawhney |
| 6,179,862 B1 | 1/2001 | Sawhney |
| 6,238,412 B1 | 5/2001 | Dubrul |
| 6,287,323 B1 | 9/2001 | Hammerslag |
| 6,302,898 B1 | 10/2001 | Edwards |
| 6,325,789 B1 | 12/2001 | Janzen |
| 6,350,274 B1 | 2/2002 | Li |
| 6,379,373 B1 | 4/2002 | Sawhney et al. |
| 6,475,177 B1 | 11/2002 | Suzuki |
| 6,514,534 B1 | 2/2003 | Sawhney |
| 6,566,406 B1 | 5/2003 | Pathak |
| 6,569,185 B2 | 5/2003 | Ungs |
| 6,605,294 B2 | 8/2003 | Sawhney |
| 6,613,070 B2 | 9/2003 | Redmond |
| 6,626,918 B1 | 9/2003 | Ginn |
| 6,635,068 B1 | 10/2003 | Dubrul |
| 6,689,148 B2 | 2/2004 | Sawhney |
| 6,703,047 B2 | 3/2004 | Sawhney |
| 6,818,008 B1 | 11/2004 | Cates |
| 6,818,018 B1 | 11/2004 | Sawhney |
| 6,887,974 B2 | 5/2005 | Pathak |
| 2001/0046518 A1 | 11/2001 | Sawhney |
| 2001/0047187 A1 | 11/2001 | Milo |
| 2001/0051813 A1 | 12/2001 | Hnojewyj |
| 2001/0053922 A1 | 12/2001 | Zhu et al. |
| 2002/0062104 A1 | 5/2002 | Ashby |
| 2002/0072767 A1 | 6/2002 | Zhu |
| 2002/0106409 A1 | 8/2002 | Sawhney |
| 2002/0114775 A1 | 8/2002 | Pathak |
| 2002/0188319 A1 | 12/2002 | Morris |
| 2003/0012734 A1 | 1/2003 | Pathak |
| 2003/0051735 A1 | 3/2003 | Pavcnik |
| 2003/0088269 A1 | 5/2003 | Ashby |
| 2003/0135198 A1 | 7/2003 | Berhow |
| 2003/0135234 A1 | 7/2003 | Fisher |
| 2003/0233120 A1 | 12/2003 | Akerfeldt |
| 2004/0122350 A1 | 6/2004 | Zhong |
| 2004/0249342 A1 | 12/2004 | Khosravi |
| 2004/0267193 A1 | 12/2004 | Bagaoisan |
| 2004/0267307 A1 | 12/2004 | Bagaoisan |
| 2004/0267308 A1 | 12/2004 | Bagaoisan |
| 2005/0149117 A1 | 7/2005 | Khosravi |
| 2007/0060950 A1 | 3/2007 | Khosravi |
| 2008/0009794 A1 | 1/2008 | Bagaoisan |

FOREIGN PATENT DOCUMENTS

| | | |
|---|---|---|
| EP | 0716833 | 6/1996 |
| WO | 9222252 | 12/1992 |
| WO | 9428798 | 12/1994 |
| WO | 9533510 | 12/1995 |
| WO | 0014155 | 3/2000 |
| WO | 0019912 | 4/2001 |
| WO | 03094749 | 11/2003 |

* cited by examiner

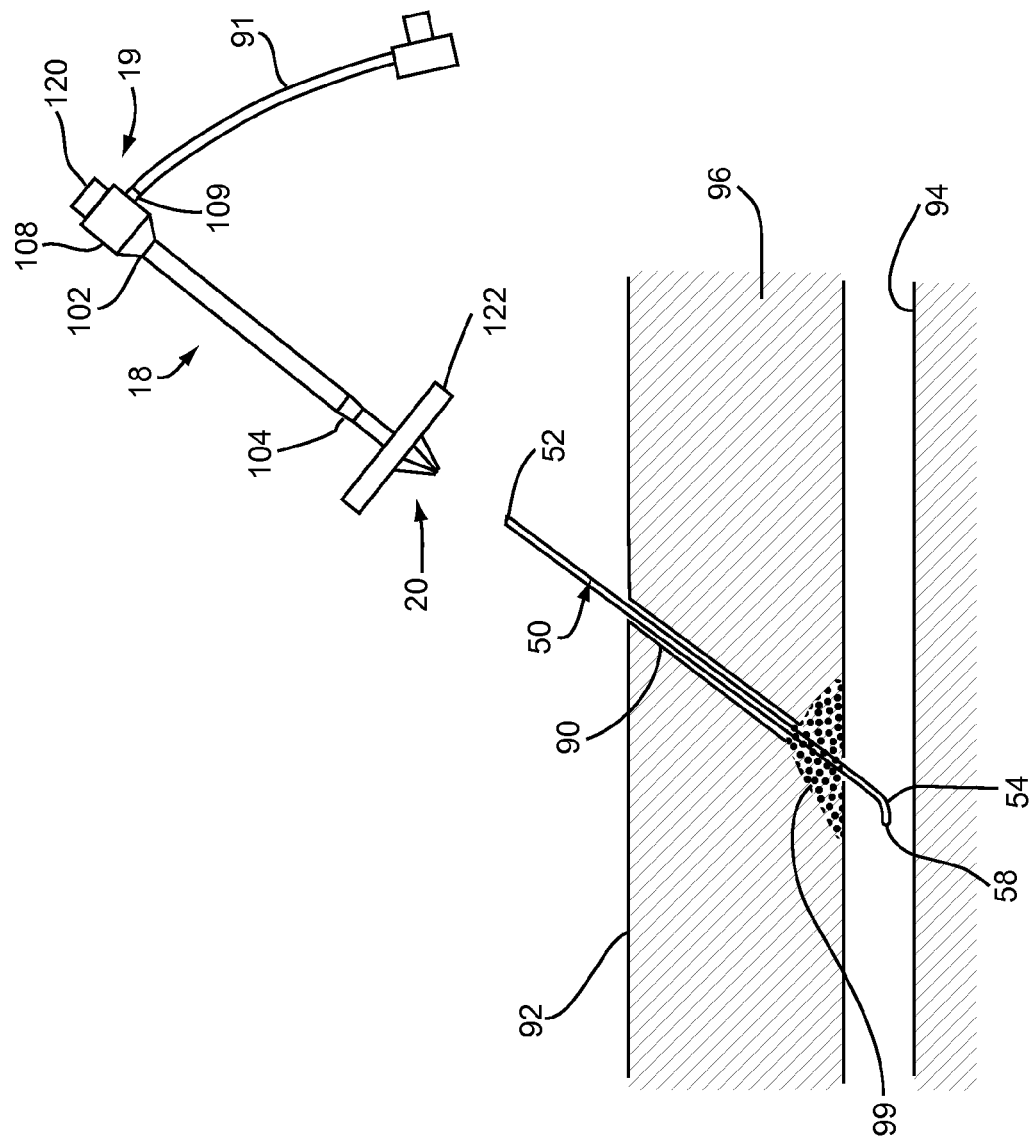

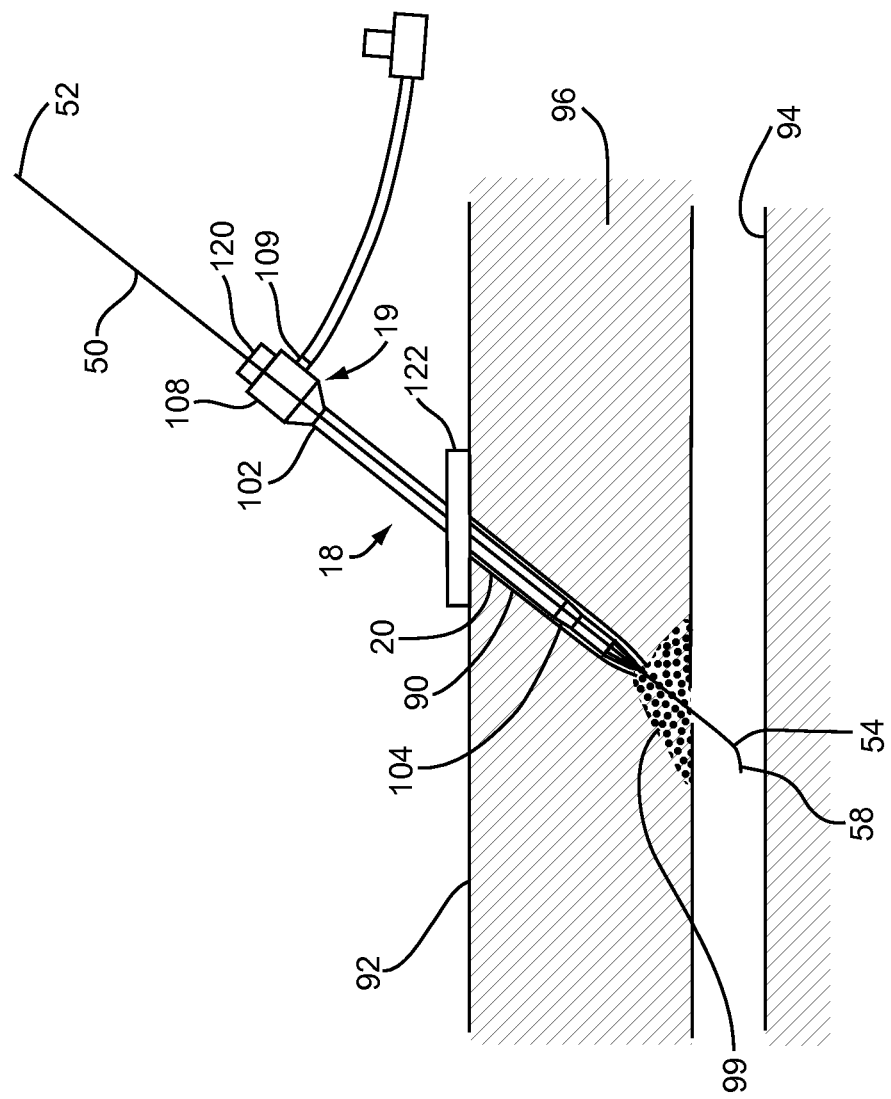

APPARATUS AND METHODS FOR SEALING A PUNCTURE IN TISSUE

RELATED APPLICATION DATA

This application is a continuation of co-pending application Ser. No. 11/112,877, filed Apr. 22, 2005, issuing as U.S. Pat. No. 8,002,742, the entire disclosure of which is expressly incorporated by reference herein.

FIELD OF INVENTION

The present invention relates generally to apparatus and methods for sealing punctures in a body, to apparatus and methods for facilitating access through a puncture extending through tissue, and, more particularly, to apparatus and methods for deploying an occlusion element, such as a balloon or other expandable member, disposed on a guidewire or other flexible elongate member, to seal a puncture through tissue.

BACKGROUND

Apparatus and methods are known for accessing a patient's vasculature percutaneously for performing a procedure within the vasculature. For example, a hollow needle may be inserted through a patient's skin and overlying tissue into a blood vessel. A guidewire is then passed through the needle into the blood vessel, whereupon the needle is removed. An introducer sheath is then advanced over the guidewire into the vessel, e.g., in conjunction with or subsequent to one or more dilators. A catheter or other device may be advanced through the introducer sheath and over the guidewire into a position for performing a medical procedure within the patient's body. In this manner, the introducer sheath facilitates introducing various instruments into the vessel, while minimizing trauma to the vessel wall and blood loss.

Upon completing the procedure, the instrument(s) and introducer sheath are removed, leaving a puncture extending between the skin and the vessel. To seal the puncture, external pressure may be applied to the overlying tissue, e.g., manually and/or using sandbags, until hemostasis occurs. This procedure, however, can be time consuming and expensive, requiring as much as an hour of a medical professional's time. It is also uncomfortable for the patient, and may require the patient to remain immobilized in an operating room, catheter lab, or holding area. In addition, a risk of hematoma exists from bleeding before hemostasis occurs.

Various apparatus and methods have been suggested for sealing a percutaneous puncture instead of or in addition to using external pressure. For example, U.S. Pat. No. 5,108,421 to Fowler discloses using a collagen plug that is delivered into a puncture through tissue. After completing the procedure, the introducer sheath and/or guidewire used to access the patient's vasculature via the puncture are removed. In one embodiment, a catheter is inserted through the puncture into the blood vessel. A balloon on the catheter is expanded and then retracted until the balloon is disposed adjacent the puncture at the wall of the vessel. A plug is then advanced into the puncture until the plug contacts the balloon, thereby preventing the plug from entering the vessel. Once the plug is positioned within the puncture, the balloon is deflated and withdrawn, leaving the plug to expand and seal the puncture and/or promote hemostasis.

By way of another example, U.S. Pat. Nos. 5,192,302 and 5,222,974 issued to Kensey et al. describe using a collagen plug that may be delivered through an introducer sheath into a puncture site.

Such sealing methods generally involve introducing plugs or other materials into the puncture after completing the procedure and removing the introducer sheath. With the introducer sheath removed, there is substantial risk of hematoma within the tissue surrounding the puncture as blood from the vessel leaks into the puncture, which may be uncomfortable and/or harmful to the patient. Further, temporary hemostasis devices for isolating the vessel from the puncture may be difficult to use effectively and/or may be expensive. Despite attempts to isolate the vessel from the puncture while delivering a plug or other sealing material, the sealing material may still leak and/or become exposed in the vessel, where the sealing material may risk causing an embolism in the vessel.

SUMMARY OF THE INVENTION

The present invention is directed generally to apparatus, systems, and methods for facilitating access through a puncture through tissue, e.g., extending from a patient's skin to a blood vessel or other body lumen, and/or for sealing such punctures. More particularly, apparatus and systems are provided that include a guidewire or other elongate tubular member having a balloon or other expandable member thereon, and methods for using such tubular members are also provided.

Generally, the expandable member may be expanded and/or collapsed by moving a piston within the tubular member to direct fluid into and/or out of the expandable member. In addition or alternatively, the expandable member may be inflated and/or deflated using a fluid dispensing device communicating with the lumen of the tubular member, e.g., that may be removably coupled to the tubular member.

In one embodiment, an occlusion member is provided for sealing a puncture. Generally, the occlusion member includes an elongate tubular member including a proximal end, a distal end, a lumen extending at least partially between the proximal and distal ends, and an expandable occlusion element disposed on a distal region of the tubular member. A piston may extend from and/or be movable within the lumen of the tubular member for directing fluid within the lumen into and/or out of the occlusion member. Such that movement of the piston relative to the tubular member may inflate and expand and/or deflate and collapse the occlusion element.

In another embodiment, a balloon wire device is provided for sealing a puncture through tissue. Generally, the device includes an elongate tubular or wire member including a proximal end, and a distal end sized and shaped for insertion into a puncture through tissue, e.g., having a profile similar to a conventional guidewire. The device includes a lumen extending axially through the wire member, and a balloon or other expandable member on a distal region of the wire member. The wire member may include one or more openings, e.g., in a proximal region of the wire member, that communicates with the lumen.

Optionally, the device may include a fluid dispensing device removably coupled to the wire member. When the fluid dispensing device is coupled to the device, fluid may be directed from the fluid dispensing device into lumen of the wire member via the opening(s) in the proximal end of the wire member. In one embodiment, the device may include a piston or other element movable within the wire member for facilitating delivery of the fluid and/or for expanding and/or collapsing the expandable member.

In another embodiment, a wire may be disposed inside the lumen having a first end affixed to the proximal end of the wire member and a second end affixed to the occlusion member. As the occlusion member is expanded, e.g., by delivering fluid into the occlusion member via the lumen of the wire member, the wire may be subjected to a compressive stress, causing the wire to buckle. Conversely, as the occlusion member is collapsed, e.g., by evacuating the fluid, the wire may extend axially to release the buckling stress, thereby extending the occlusion member as it collapses. In one embodiment, the wire may be formed from an elastic or superelastic material, allowing the wire to resiliently buckle and extend.

In yet another embodiment, a system is provided for introducing one or more instruments into a body lumen of a patient through a puncture extending from the patient's skin to the body lumen. Generally, the system includes a balloon wire or other occlusion member, such as those described above. In addition, the system may include a fluid dispensing device, an assembly for delivering a sealing compound into the puncture, and/or an introducer sheath.

The fluid dispensing device may be removably coupled to the occlusion member, e.g., for delivering fluid from the fluid dispensing device into a lumen of the occlusion member. The introducer sheath may include a proximal end, a distal end sized and shaped for insertion into the puncture, and a lumen extending between the proximal end and an opening in the distal end.

In accordance with another embodiment, a method is provided for sealing a puncture in a vessel using an occlusion member including an elongate tubular or wire member having a proximal end, a distal end, a lumen extending at least partially therebetween, and an expandable occlusion member on a distal region of the tubular member.

Generally, the distal end of the tubular member is introduced into a puncture through tissue with the occlusion member collapsed, e.g., until the occlusion member is disposed within a body lumen communicating with the puncture. A piston within the tubular member is moved to deliver fluid within the tubular member into the occlusion member, causing the occlusion member to expand. The tubular member may be at least partially refracted until the expanded occlusion member substantially seals the body lumen from the puncture.

In another embodiment, a method is provided for sealing a puncture in a wall of a blood vessel or other body lumen using an occlusion member including an elongate tubular member and an expandable occlusion member on a distal region of the tubular member. A fluid dispensing device may be coupled or otherwise provided on a proximal end of the tubular member. The distal end of the tubular member may be introduced through the puncture with the occlusion member collapsed. Fluid may be dispensed into the tubular member from the fluid dispensing device to expand the occlusion member. The expanded occlusion member may be retracted against the wall of the body lumen to substantially seal the puncture.

In accordance with still another aspect of the invention, a method is provided for preparing an occlusion member, the occlusion member comprising an elongate tubular member including a proximal end, a distal end having an inflatable occlusion element thereon, a lumen extending between the proximal and distal ends communicating with an interior of the occlusion element, and an opening at an intermediate location on the tubular member communicating with the lumen. In one embodiment, the method includes advancing a distal end of an elongate member into the proximal end of the tubular member until the distal end of the elongate member is disposed proximal to the opening and a proximal end of the elongate member extends proximally from the tubular member; evacuating air from within the lumen and the interior of the occlusion member via the opening; delivering a substantially incompressible inflation media into the lumen without substantially expanding the occlusion element; and advancing the distal end of the elongate member distally beyond the opening to substantially isolate the lumen with the fluid therein without substantially expanding the occlusion element. The method may further include advancing the elongate member distally within the tubular member to expand the occlusion element.

Other aspects and features of the invention will become apparent from consideration of the following description taken in conjunction with the accompanying drawings.

BRIEF DESCRIPTION OF THE DRAWINGS

The drawings illustrate exemplary embodiments of the invention, in which:

FIGS. 4A-4C are cross-sectional views of a patient's body, showing a method for delivering a sleeve and introducer sheath into the puncture of FIGS. 3A-3C after delivering a sealing compound therein.

DETAILED DESCRIPTION OF THE ILLUSTRATED EMBODIMENTS

Figure 1:
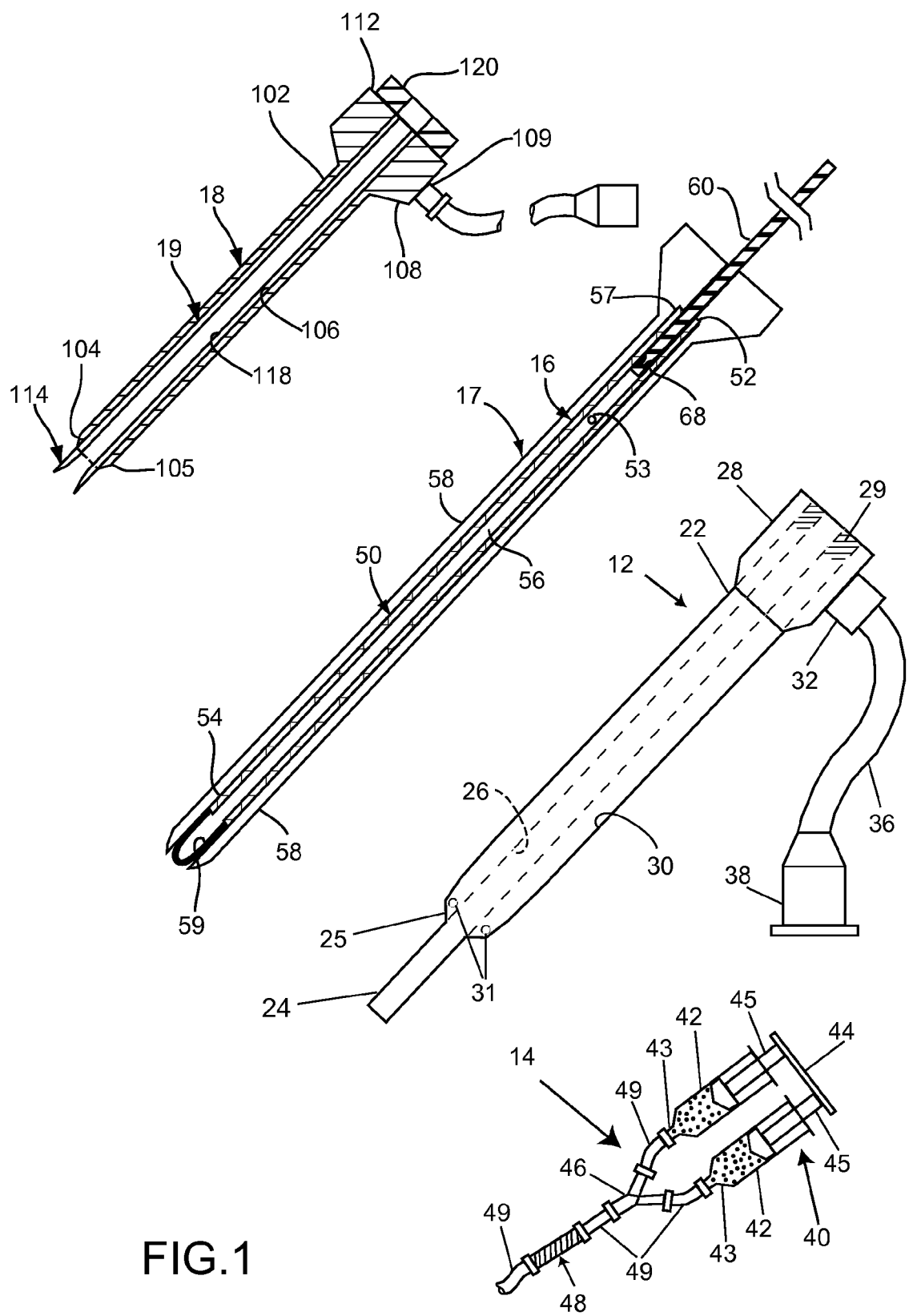
FIG. 1 is a side view of a system for sealing a puncture, including an introducer sheath, an occlusion member, a delivery sheath, and a syringe assembly for delivering sealing compound via the delivery sheath.

Turning to the drawings, FIG. 1 shows an exemplary embodiment of a system 10 for accessing and/or delivering sealing compound into a puncture through tissue, e.g., a percutaneous puncture communicating from a patient's skin through intervening tissue to a blood vessel or other body lumen (not shown). Generally, the system 10 includes a delivery or injection sheath 12, a source of sealing compound 14, and an occlusion member 16. Optionally, the system 10 may include other components, e.g., an introducer or procedure sheath 18 (separate from the delivery sheath 12), and one or more dilators (an exemplary dilator 19 being shown). The system 10 may also include one or more of a needle for creating the puncture, a guidewire, and/or one or more sections of tubing (not shown). In addition or alternatively, the system 10 may include other components for creating the puncture, introducing the delivery sheath 12 and/or guidewire into a body lumen, and/or accessing the vessel, e.g., for introducing instruments (not shown) into the vessel via the puncture.

Generally, the delivery sheath 12 is an elongate tubular member, including a proximal end 22, a distal end 24, and a primary or guidewire lumen 26 extending between the proximal and distal ends 22, 24. In addition, the delivery sheath 12 may include one or more secondary or injection lumens 30 that extend from the proximal end 22 to one or more outlets (e.g., two outlets 31, as shown) in the wall of the delivery sheath 12.

As shown, a single secondary lumen 30 is disposed concentrically around the primary lumen 26. Alternatively, one or more secondary lumens (not shown) may be formed or otherwise provided in the wall of the delivery sheath 12, e.g., in a side-by-side arrangement. The primary lumen 26 may be of sufficient size to accommodate sliding a guidewire therethrough, e.g., between about 0.014 and 0.018 inch (0.35-0.45 mm) diameter, while the secondary lumen 30 may be of sufficient size to accommodate delivering sealing compound therethrough.

The secondary lumen 30 extends from a housing 28 on the proximal end 22 of the delivery sheath 12 to an intermediate portion 25 between the proximal and distal ends 22, 24. As shown, the intermediate portion 25 tapers where the secondary lumen 30 terminates, with the delivery sheath 12 having a smaller diameter from the intermediate portion 25 to the distal end 24 (e.g., since only the primary lumen 26 extends along this portion of the delivery sheath 12). The smaller diameter distal portion may have a desired length, e.g., at least about five millimeters (5 mm). The outlet(s) 31 may be provided on the intermediate portion 25, e.g., where the delivery sheath 12 tapers, which may facilitate directing the sealing compound delivered through the secondary lumen 30 radially outwardly away from the delivery sheath 12.

The housing 28 may be attached to or otherwise provided on the proximal end 22 of the delivery sheath 12. The housing 28 may include one or more side ports (e.g., one side port 32, as shown) that communicate with an interior of the housing 28 and the secondary lumen 30 of the delivery sheath 12. The housing 28 may include one or more seals 29 to seal the interior of the housing 28, e.g., such that sealing compound delivered from the side port 32 may be directed through the secondary lumen 30. Optionally, the housing 28 may also include one or more seals (not shown), e.g., a hemostatic seal, for sealing the primary lumen 26 while accommodating inserting a needle, guidewire, occlusion member, or other instrument (not shown) into the lumen 26, e.g., preventing bodily fluids, such as blood, from escaping proximally through the delivery sheath 12, as is known in the art.

A section of flexible tubing 36 may be connected to or otherwise extend from the side port 32 to a luer lock adapter 38, a manual shut-off valve (not shown), and/or other connector (also not shown), e.g., to facilitate connecting tubing and the like (also not shown) to the side port 32. For example, a source of sealing compound, such as the dual-syringe assembly 40 described below, may be connected to the luer lock adapter 38 before or during a procedure.

In alternative embodiments, the delivery sheath may be a tubular member including a single lumen (not shown), which may include a hub, side port, and/or other components, similar to the embodiment described above. Additional information on such delivery sheaths may be found in co-pending application Ser. No. 10/454,362, filed Jun. 4, 2003 and Ser. No. 10/745,946, filed Dec. 24, 2003. The entire disclosures of these references and any others cited therein are expressly incorporated herein by reference.

Returning to FIG. 1, the occlusion member 16 may include an elongate wire member or other tubular body 50 carrying a balloon or other expandable member 58. The wire member 50 generally includes a proximal end 52, a distal end 54, and a lumen 56 extending at least partially between the proximal and distal ends 52, 54. The wire member 50 may have an outer diameter of about 0.008 to 0.038 inch, e.g., not more than about 0.040 inch. The wire member 50 may be substantially flexible or semi-rigid, e.g., to allow the wire member 50 to curve, bend, or otherwise adapt to anatomy through which it is advanced, yet have sufficient column strength to accommodate advancing the distal end 54 by pushing on the proximal end 52.

In one embodiment, the wire member 50 may be formed from one or more wire coil(s) (not shown) wound into an elongate tubular shape, similar to a guidewire. The wire coil(s) may be formed from one or more substantially round, square, or flat wires, e.g., made from stainless steel, Nitinol, or other metal. Thus, the wire member 50 may be substantially flexible yet may be pushed form the proximal end 52 without substantial risk of kinking or buckling.

The wire member 50 may include material applied to the wire coil(s), e.g., a polymer or other coating, to create a substantially nonporous wall such that fluid may be contained within the lumen 56 without substantial leaking. For example, a liquid polymer or other material may be applied to the outer and/or inner surfaces of the wire coil(s), e.g., by dipping the entire wire coil(s), brushing, and/or spraying material onto the coiled wire(s), or by applying a coating to the wire(s) using such methods before the wire(s) are formed into the wire coil(s). If appropriate, the coating material may be cured or otherwise solidified using known procedures. Thus, coating material may have sufficient flexibility to allow the wire coil(s) to flex as the wire member 50 bends while maintaining the coating integrity and nonporous wall.

In another embodiment, the wire member 50 may be formed from a solid-walled tube, such as a section of thin-walled hypo-tube. Exemplary materials for the wire member 50 include stainless steel, Nitinol, or other metal, polyimide or other plastic tubing, and/or composite materials.

Figure 2A:
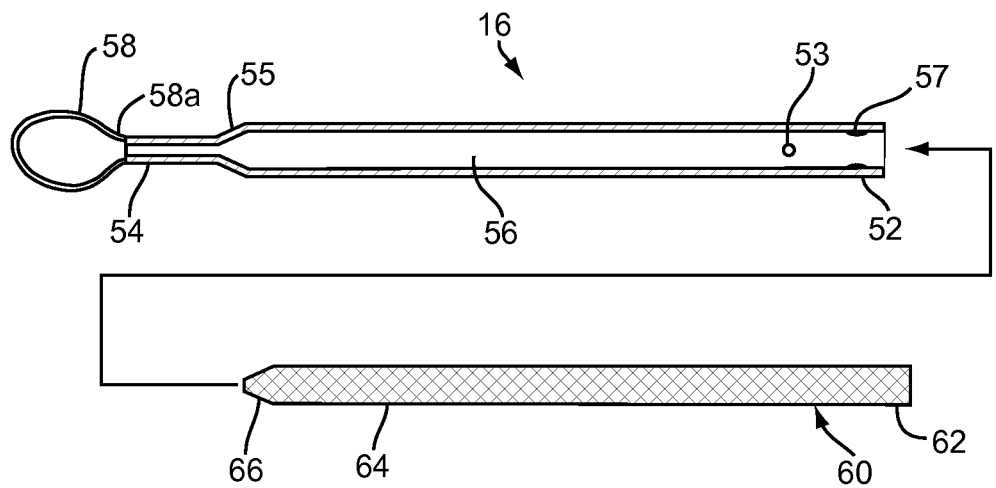
FIGS. 2A and 2B are cross-sectional side views of the occlusion member of FIG. 1, showing a method for assembling the occlusion member.
Figure 2B:
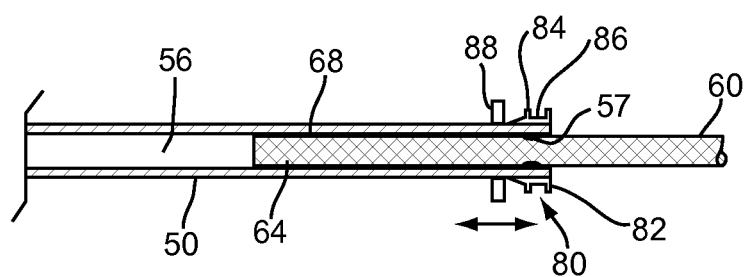
Figure 3A:
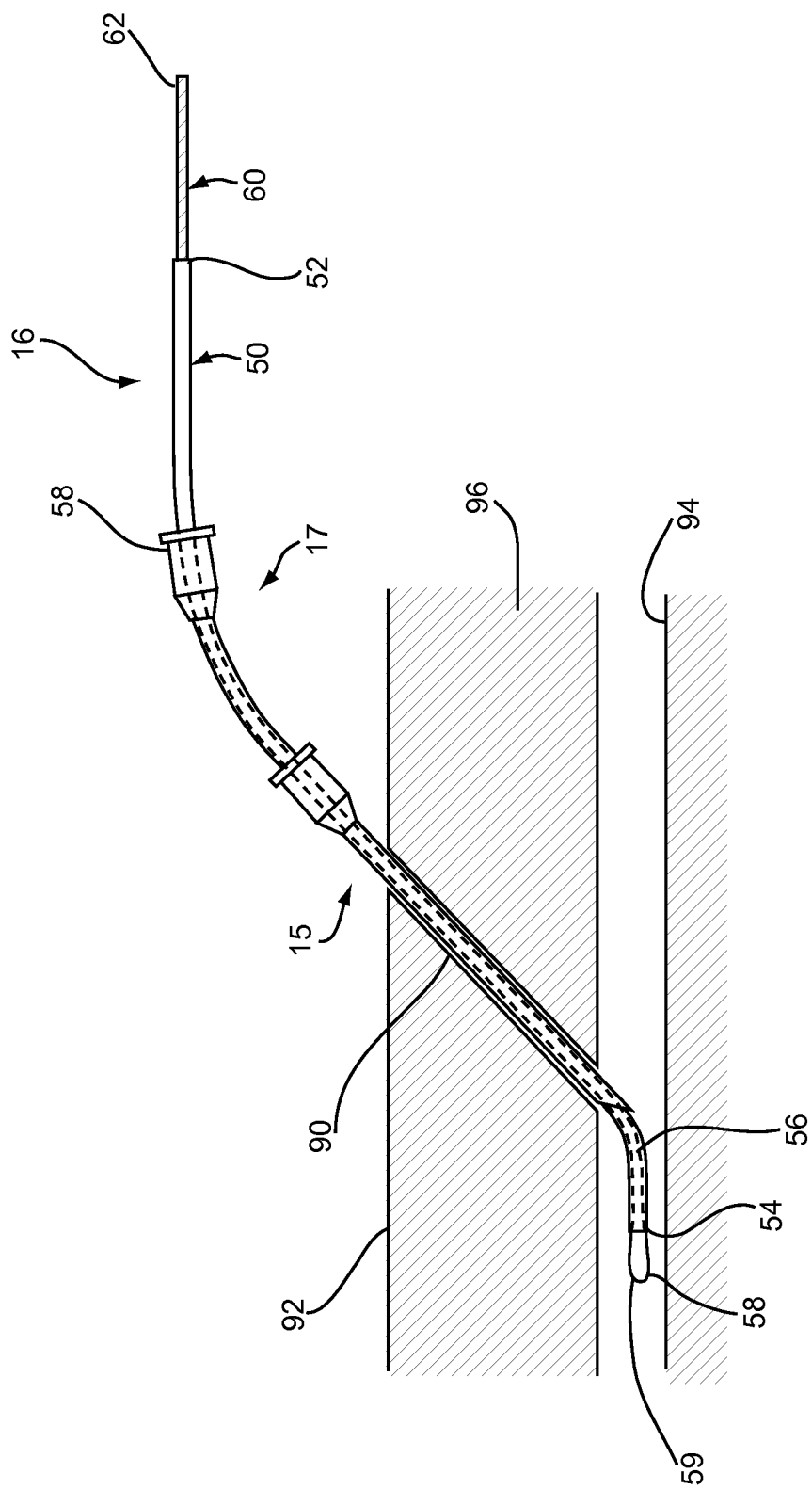
FIGS. 3A-3C are cross-sectional views of a patient's body, illustrating a method for delivering a sealing compound a puncture extending between the patient's skin and a blood vessel.

Returning to FIG. 1, with additional references to FIGS. 2A and 2B, the balloon 58 may be expandable from a collapsed state (such as that shown in FIG. 1) to an enlarged state (such as that shown in FIG. 3A). For example, saline, air, or other fluid may be introduced into an interior 59 of the balloon 58 to expand the balloon 58 from the collapsed state to the enlarged state.

In one embodiment, the balloon 58 may be formed from a flexible, substantially inelastic material, e.g., a nonelastomeric material, such as PET, nylon, polyethylene, polyurethane, PEBAX, and the like. Thus, the balloon 58 may be substantially noncompliant or semi-compliant, thereby expanding to a predetermined size once a minimum pressure is introduced into the interior 59 of the balloon 58. Alternatively, the balloon 58 may be formed from an elastic material, such that the size of the balloon 58 in the expanded state is dependent upon the pressure or volume of fluid delivered into the balloon 58. Additional information on balloons that may be used are disclosed in co-pending application Ser. No. 10/454,362, incorporated above, and Ser. No. 10/806,927, filed Mar. 22, 2004, the entire disclosure of which is also expressly incorporated herein by reference.

Figure 5A:
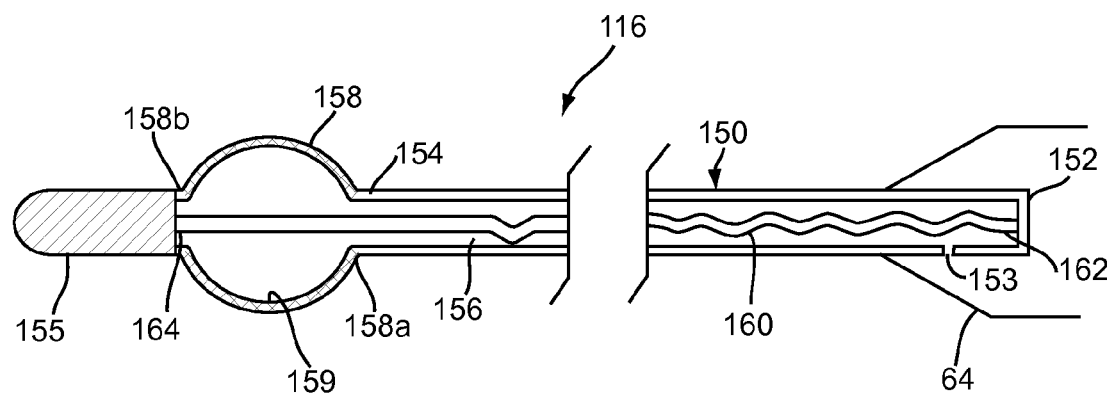
FIGS. 5A and 5B are cross-sectional side views of another embodiment of an occlusion member including a balloon in an expanded (i.e., deployed) state and a collapsed (i.e., un-deployed) state, respectively.
Figure 5B:
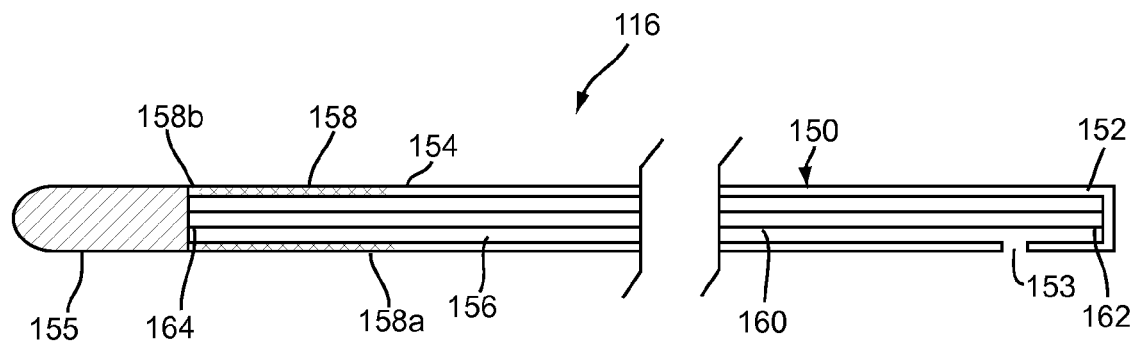

As shown in FIG. 2A, the balloon 58 may be an enclosed expandable body with an open end 58a. The open end 58a may be attached to the distal end 54 of the wire member 50 such that the balloon 58 extends distally from the distal end 54 of the wire member 50. For example, the end 58a may be bonded to the distal end 54 and/or may be attached using a band (not shown) secured around the distal end 54 and the open end 58a of the balloon 58. The interior 59 of the balloon 58 thereby communicates with the lumen 56 of the wire member 50 such that fluid from the lumen 56 may be used to expand the balloon 58, as explained further below. Alternatively, as seen in FIGS. 5A and 5B, an occlusion member 116 may include a balloon 158 disposed proximal to a distal tip 155 of the occlusion member 116, as described further below.

Figure 2C:
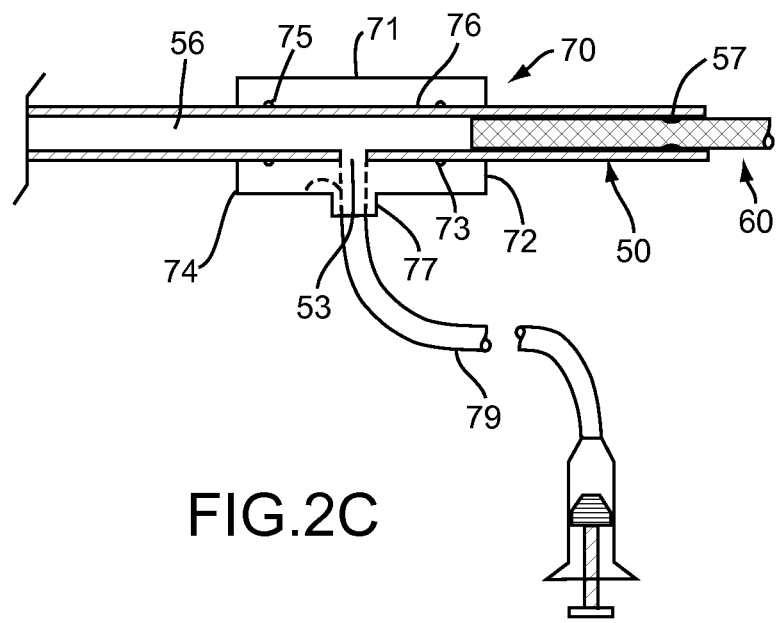
FIGS. 2C and 2D are cross-sectional details of the occlusion member of FIG. 1, showing a fluid dispensing device for delivering fluid into a wire member of the occlusion member.

Returning to FIG. 1, with additional reference to FIGS. 2A-2C, the wire member 50 may include one or more ports or other openings 53 located in an intermediate region of the wire member 50. The port(s) 53 may simply be one or more holes formed in the side wall of the wire member 50, e.g., by laser cutting, drilling, etching, and the like. The port(s) 53 communicate with the lumen 56, e.g., allowing a fluid source (not shown) to communicate with the lumen 56 from the outside environment surrounding the wire member 50.

The wire member 50 also includes a rod, tube, or other piston 60 slidable into and out of the lumen 56 from the proximal end 52 of the wire member 50. The piston 60 may be an elongate member including a proximal end 62, and a distal end 64 that is axially moveable within the lumen 56 of the wire member 50. The piston 60 may be pushed or pulled, e.g., to either advance or retract the distal end 64 within the lumen 56 of the wire member 50.

The piston 60 may be formed from a substantially flexible or semi-rigid material, similar to the wire member 50, e.g., having sufficient column strength to allow the distal end 64 to be advanced into the wire member 50 by pushing on the proximal end 62. For example, the piston 60 may be an elongate wire coil, similar to the wire member 50, or alternatively a solid wire or other filament. In one embodiment, the piston 60 may have a substantially uniform profile along its entire length, e.g., having a diameter between about 0.005 to 0.035 inch, such that the distal end 64 may be slidably received in the lumen 54 of the wire member 50.

Optionally, a lubricous, low-friction, or other coating (not shown) may be applied to an exterior surface of the piston 60, e.g., on at least the distal end 64. In addition or alternatively, a similar or different coating (also not shown) may be applied to at least a portion of an interior surface of the wire member 50. The coating may reduce or increase the force needed to cause axial movement of the piston 60 within the lumen 56 of the wire member 50, depending upon the resistance desired.

A fluid-tight seal may also be provided between the piston 60 and the wire member 50, e.g., to substantially seal the lumen 56 of the wire member 50 such that fluid within the lumen 56 may not leak between the wire member 50 and the piston 60, e.g., proximally out the proximal end 52 of the wire member 50. For example, as shown in FIGS. 1 and 2A-2D, a seal 68 may be provided on the distal end 64 of the piston 60, e.g., attached to the distal end 64 and/or disposed on an exterior of the piston 60 at or adjacent the distal end 64. In addition or alternatively, a seal 57 may be provided on an interior surface of the wire member 50. The seals 57 and/or 68 may provide a fluid-tight seal inside the wire member 50 to retain fluid within the lumen 56 and balloon 58 once the distal end 64 of the piston 60 has moved distally past the port(s) 53, as described further below.

Optionally, as seen in FIG. 1, the occlusion member 16 may also include a retaining sheath or other constraint 17 slidable over the wire member 50, e.g., for maintaining the balloon 58 in its collapsed condition and/or for facilitating advancing the occlusion member 16 into a puncture through tissue. For example, the retaining sheath 17 may be an elongate tubular member including proximal and distal ends, and a lumen extending therebetween. A hub may be located on the proximal end, e.g., to facilitate manipulating the retaining sheath 17. The retaining sheath 17 may have a diameter or other size to allow the distal end to be inserted into and/or through the primary lumen 26 of the delivery sheath 12. The hub of the retaining sheath 17 may be larger than the size of the primary lumen 26, e.g., to provide a stop limiting distal advancement of the retaining sheath 17 into the delivery sheath 12. The retaining sheath 58 may be sufficiently flexible to conform to the surrounding anatomy, e.g., when the retaining sheath 58 is inserted into or removed from a puncture, e.g., along with other components.

Referring to FIG. 2A, in one embodiment, the wire member 50 may include a tapered region 55 located proximal to the balloon 58. Correspondingly, the distal end 64 of the piston 60 may include a shoulder or tapered distal tip 66 angled to conform to the tapered region 55 of the wire member 50. The tapered region 55 may act as an abutment to limit advancement of the piston 60 within the wire member 50. In addition, the shoulder 66 may engage the tapered region 55, e.g., by friction or interference fit, to restrict proximal movement of the piston 60 relative to the wire member 50, as explained further below.

Further, this configuration may provide tactile feedback to the user, e.g., that the balloon 58 has been fully expanded. For example, the tapered region 55 may be provided a predetermined distance from the port(s) 53, thereby defining a volume of fluid within the lumen 56 that may be directed into the balloon 58 when the distal end 64 of the piston 60 is advanced from its loaded position (described below) into engagement with the tapered region 55. The volume that is displaced may be determined to be the desired volume for sufficiently inflating and expanding the balloon 58.

In alternative embodiments, the piston 60 and/or wire member 50 may include other lock elements (not shown) for securing the piston 60 relative to the wire member 50. For example, the piston 60 may include one or more ramps, tabs, or other detents (not shown), e.g., on the distal end 64, and the wire member 50 may include one or more mating ramps, tabs, or other detents (also not shown), e.g., within the lumen 56. When the piston 60 is advanced a predetermined distance into the wire member 50, e.g., until the distal end 64 of the piston 60 is disposed adjacent to the distal end 54 of the wire member 50 but proximal to the balloon 58, the detents may interlock, preventing the piston 60 from being withdrawn proximally.

For example, the lock element(s) may act as a ratchet, e.g., allowing the piston 60 to be advanced distally but not retraced proximally until a final distal position is attained. Such lock element(s) may also provide tactile and/or audio feedback to the user, allowing the user to determine when the piston 60 has reached a desired position, e.g., corresponding to complete expansion of the balloon 58, as described further below. Optionally, the lock element(s) may be overcome by pulling on the piston 60, e.g., using a predetermined force sufficient to disconnect or even break the lock securing the piston 60. Once the lock is broken, the lock elements may prevent the piston 60 from being reinserted into the wire member 50, e.g., to prevent reuse of the occlusion member 16.

Figure 2D:
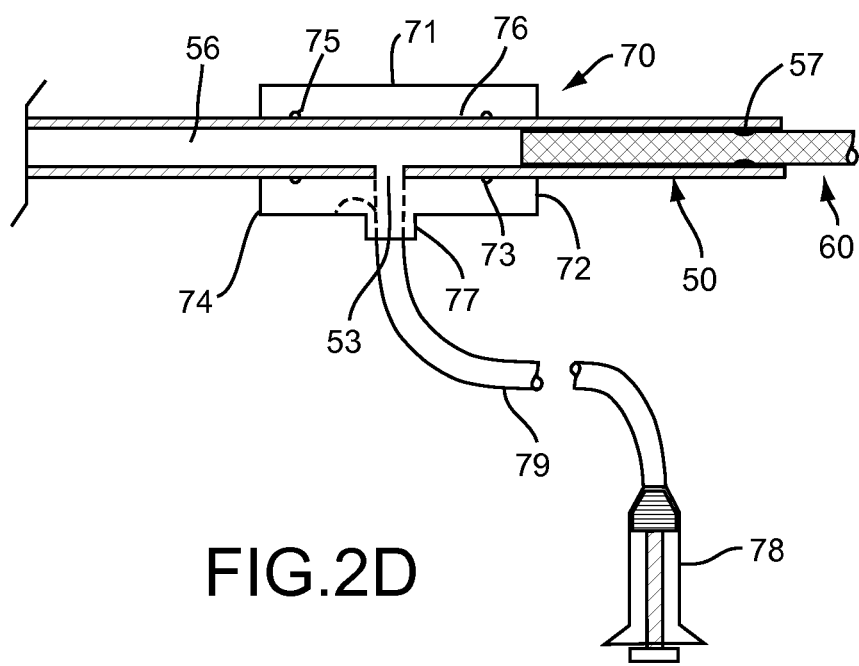

Turning to FIGS. 2C and 2D, a fluid loading device or housing 70 is shown for loading fluid into the lumen 56 of the wire member 50. In the embodiment shown, the fluid loading device 70 includes a barrel or other housing 71 including first and second ends 72, 74, and a lumen 76 extending between the first and second ends 72, 74. The housing 71 also includes a side port 77 communicating with the lumen 76. In addition, the fluid loading device 70 includes a source of vacuum and/or a source of fluid, such as one or more syringes (one syringe 78 shown) connectable to the side port 77 by tubing 79. The fluid within the syringe 78 may be a substantially incompressible liquid, such as water, saline, and the like, or a gas, such as air, nitrogen, carbon dioxide, and the like.

The housing 71 has a size such that the housing 71 may be received around the occlusion member 16, e.g., by inserting one end of the wire member 50 into the lumen 76 of the housing 70. The housing 71 may include one or more seals to provide a fluid-tight seal between the housing 71 and the wire member 50. As shown, the housing 71 includes an annular seal 73, 75 adjacent each of the first and second ends 72, 74 of the housing 71, i.e., extending from an internal surface of the housing 71 against the external surface of the wire member 50.

Turning to FIGS. 2A-2D, a method is shown for loading fluid into the occlusion member 16 using the fluid loading device 70, e.g., before or during a medical procedure. As shown in FIG. 2A, the wire member 50 and piston 60 may be provided separately initially, e.g., in a kit along with one or more other components of the system 10, such as the fluid loading device 70 and/or the other components described herein. Alternatively, the occlusion member 16 may be provided at least partially assembled, e.g., using one of the procedures described below, which may be performed at a manufacturing location or at one or more other locations between the original manufacturing facility and the site of a procedure where the occlusion member 16 may be used.

Turning to FIG. 2B, the occlusion member 16 may be assembled by inserting the distal end 64 of the piston 60 into the proximal end 52 of the wire member 50. Consequently, the piston 50 may be directed into the lumen 56, e.g., until the distal end 64 of the piston 60 is located proximal to the port(s) 53 in the wire member 50.

The housing 71 of the fluid loading device 70 may then be directed over the wire member 50. The seals 73, 75 of the housing 71 may slide along the exterior surface of the wire member 50 as the housing 71 is directed along the wire member 50. When the housing 71 overlies the port(s) 53, the seals 73, 75 may straddle the port(s) 53 such that the lumen 76 of the housing 71, and consequently the side port 77, communicate with the lumen 56 of the wire member 50 via the port(s) 53. Alternatively, the piston 60 may be advanced into the wire member 50 after the housing 71 is placed around the wire member 50 over the port(s) 53, e.g., until the distal end 64 is disposed proximal to the port(s) 53.

With the housing 71 and piston 60 loaded on and in the wire member 50, the lumen 56 of the wire member 50 may contain air or other gases. These gases may be evacuated from the lumen 56 by connecting a source of vacuum to the side port 77 of the housing 71. For example, a syringe 78 may be connected, e.g., by tubing 79 to the side port 77. The syringe 78 may then be drawn to substantially aspirate the air from within the lumen 56 of the wire member 50. Alternatively, a vacuum line and the like (not shown) may be used to evacuate the air out of the lumen 56 and balloon 58. Once the air is evacuated from the lumen 56, a valve (not shown) on the tubing 79 or a connector on the side port 77 (not shown) may be closed to maintain the vacuum within the lumen 56.

A source of fluid, e.g., another syringe filled with fluid (represented by syringe 78, although a different syringe may be used), may be coupled to the side port 77, e.g., via tubing 79 for delivering fluid into the lumen 56 of the wire member 50. The syringe 78 may be depressed to deliver sufficient fluid into the lumen 56 via the port(s) 53 to substantially fill the lumen 56. The fluid is preferably delivered into the lumen 56 in such a manner so as to not cause deployment or expansion of the balloon 58, i.e., such that the balloon 58 remains substantially collapsed.

Once the lumen 56 has been sufficiently filled with fluid, the piston 60 may be advanced distally until the distal end 64 is disposed distal to the port(s) 53. Because of the seal 68 on the piston 60, the lumen 56 and interior 59 of the balloon 58 may become substantially isolated from the port(s) 53 and therefore from the surroundings around the wire member 50. The housing 71 may then be removed from around the wire member 50, e.g., by sliding the housing 71 down and off the end of the wire member 50, without fluid leaking.

The piston 60 may only be advanced a relatively short distance, e.g., such that the seal 68 is located just beyond the port(s) 53. This may minimize any expansion of the balloon 58, which may occur as the piston 60 displaces fluid within the lumen 56 into the interior 59 of the balloon 58. In addition or alternatively, the volume of fluid delivered into the lumen 56 using the fluid loading device 70 may be reduced slightly, i.e., to maintain a slight vacuum within the lumen 56. When the distal end 64 of the piston 60 is advanced past the side port(s) 53, the volume displaced may correspond to the residual vacuum. This may reduce the risk of the balloon 58 expanding undesirably when the piston 60 is advanced to isolate the lumen 56.

Optionally, as shown in FIG. 2B, the occlusion member 16 may include a locking device 80, which may be used to selectively restrain the piston 60 from moving axially relative to the wire member 50. As shown, the locking device 80 may include an annular member 82 attached or otherwise fixed to the proximal end 52 of the wire member. 50. The annular member 82 may include a ramped distal surface 84 leading to a recessed abutment 86. The locking device 80 may also a locking ring 88 disposed distal to the annular member 82 and slidable along an exterior surface of the wire member 14. For example, the locking ring 88 may be directed axially, e.g., proximally, until it slidably engages the ramped distal surface 84 and enters the recessed abutment 86.

The locking ring 88 may compress the annular member 82 inwardly as it slides along the ramped distal surface 84, thereby compressing the proximal end 52 of the wire member 50 inwardly against the piston 55, e.g., to crimp the wire member 50 against the piston 60 or otherwise frictionally engage the wire member 50 and piston 60 together. Thus, substantial axial movement of the piston 60, distally or proximally, relative to the wire member 50 may be prevented using the locking device 80.

To allow movement of the piston 60, the locking ring 88 may be disengaged from the recessed abutment 86 by pushing the locking ring 88 distally out of the recessed abutment 84 and down the ramped distal surface 86. Once the locking ring 88 is disengaged, the piston 60 may be free to move axially within the wire member 50.

Alternatively, the locking device may include other locking mechanisms, such as one or more clips, retainers, and the like that may be activated to prevent substantial axial movement of the piston 60 relative to the wire member 50 while the locking device is engaged.

Returning to FIG. 1, the system 10 may also include a source of sealing compound 14, such as a dual syringe assembly 40 or other delivery device (not shown), e.g., that includes two components of a sealing compound. As shown, the syringe assembly 40 includes a pair of syringe barrels 42, including outlets 43 and a plunger assembly 44 slidable into the barrels 42 to cause the components therein to be delivered through the outlets 43. In the embodiment shown, the plunger assembly 44 includes a pair of plungers 45 coupled to one another that are received in respective barrels 42. In this manner, both plungers 45 may be manually depressed substantially simultaneously to deliver the components together from the syringe barrels 42. Alternatively, a system for automatically advancing the plungers 45 and/or otherwise delivering the components in the barrels 42 may be used, such as those disclosed in co-pending application Ser. No. 10/806, 934, filed Mar. 22, 2004, the entire disclosure of which is expressly incorporated herein by reference.

Optionally, the delivery device 14 may include a "Y" fitting 46, a static mixer 48, and/or tubing 49, e.g., for connecting the "Y" fitting 48 to outlets 43 of the barrels 42, the mixer 48 to the "Y" fitting 46 and/or to the side port 32 of the delivery sheath 12, such that the sealing components ejected out of the barrels 42 may mix before being directed into the side port 32 of the delivery sheath 12. The outlets 43, "Y" fitting 46, mixer 48, and/or tubing 49 may include cooperating connectors, e.g., luer lock connectors and the like (not shown), for connecting them together.

Respective sealing components may be provided in each syringe barrel 42 of the syringe assembly 40 that, when mixed together, are activated to form a hydrogel or other sealing compound. Additional information on such hydrogels and systems for delivering them are disclosed in U.S. Pat. Nos. 6,152,943, 6,165,201, 6,179,862, 6,514,534, and 6,379,373, and in co-pending applications publication Nos. 2002-0106409 published on Aug. 8, 2002, 2003-0012734 published on Jan. 16, 2003, 2002-0114775 published on Aug. 22, 2002, and 2004-0249342 published on Dec. 9, 2004. The disclosures of these references and any others cited therein are expressly incorporated by reference herein.

With continued reference to FIG. 1, the system 10 may also include an introducer sheath 18. As shown, the introducer sheath 18 is an elongate tubular member including a proximal end 102, a distal end 104, and a lumen 106 extending between the proximal and distal ends 102, 104. The introducer sheath 18 may terminate in a tapered distal tip 105 for facilitating advancing the introducer sheath 18 substantially atraumatically through tissue into a puncture. Exemplary materials for the introducer sheath 18 may include one or more plastics, such as FEP, polyvinyl chloride (PVC), polyamide, PEEK, nylon, PET, PEBAX, and polyethylene, metals, such as stainless steel, and nickel titanium, and/or composite materials. The introducer sheath 18 may be substantially rigid, semi-rigid, or substantially flexible, e.g., to facilitate insertion through a puncture into a blood vessel or other body lumen. The introducer sheath 18 may have an outer diameter between about 0.080 to 0.140 inch and/or a wall thickness between about 0.002 to 0.10 inch.

A housing 108 may be attached to or otherwise provided on the proximal end of the introducer sheath 18. The housing may include a side port 109 that communicates with an interior of the housing 108 and the lumen 106 of the introducer sheath 18. A section of flexible tubing may be connected to or otherwise extend from the side port 109, terminating in a manual shut-off valve and/or a luer lock or other connector (not shown), e.g., to facilitate connecting tubing and the like (not shown) to the side port 109. The housing 108 may also include one or more seals (not shown), e.g., a hemostatic seal, for substantially sealing the lumen of the delivery sheath 18, yet accommodating inserting one or more instruments (not shown) into the lumen.

Optionally, a dilator 19 may also be provided, e.g., within the lumen 86 of the introducer sheath 18. The dilator 19 may also include a proximal end 112, a distal end 114 sized for insertion through the lumen of the introducer sheath 18, a lumen 118 extending between the proximal end distal ends, and a hub or other handle 120 on the proximal end 112. The distal end 114 may include a tapered or multiple ramped shape, similar to known dilators. The dilator 19 may be formed from substantially rigid, semi-rigid, or substantially flexible materials, similar to the introducer sheath 18.

The dilator 19 may be loaded into the introducer sheath 18 during manufacturing or immediately before a procedure. In addition, the dilator 19 may be loaded into the introducer sheath 18 by inserting the distal end 114 of the dilator 19 into the hub 108 and lumen 106 of the introducer sheath 18 until the hubs 108, 120 abut one another. Once inserted into the introducer sheath 18, the distal end 114 of the dilator 19 may extend beyond the distal end 104 of the introducer sheath 18, e.g., to provide a gradually tapering transition for the assembly. Thus, before a procedure, the dilator 19 and introducer sheath 18 may be disposed concentrically around one another in an assembly, as shown in FIG. 1. Optionally, the dilator 19 may be eliminated, if desired.

In one embodiment, a flexible and/or thin-walled sleeve 20, similar to those disclosed in U.S. application Ser. No. 11/112, 970, entitled "Apparatus and Methods For Facilitating Access Through A Puncture Including Sealing compound Therein," filed Apr. 22, 2005, may also be used in connection with the introducer sheath 18. The entire disclosure of this application is expressly incorporated by reference herein.

Turning to FIGS. 3A-3C and 4A-4C, a method is shown for delivering an introducer sheath (and/or sleeve), such as the introducer sheath 18 described above, into a passage 90 extending through tissue 96. In the illustrated embodiment, the passage 90 is a percutaneous puncture extending from a patient's skin 92 to a blood vessel or other body lumen 94. For example, the vessel 94 may be a peripheral artery, e.g., a femoral artery, a carotid artery, and the like. It will be appreciated that systems and methods constructed and undertaken as described herein may be used to seal other passages through tissue within a patient's body.

Figure 3B:
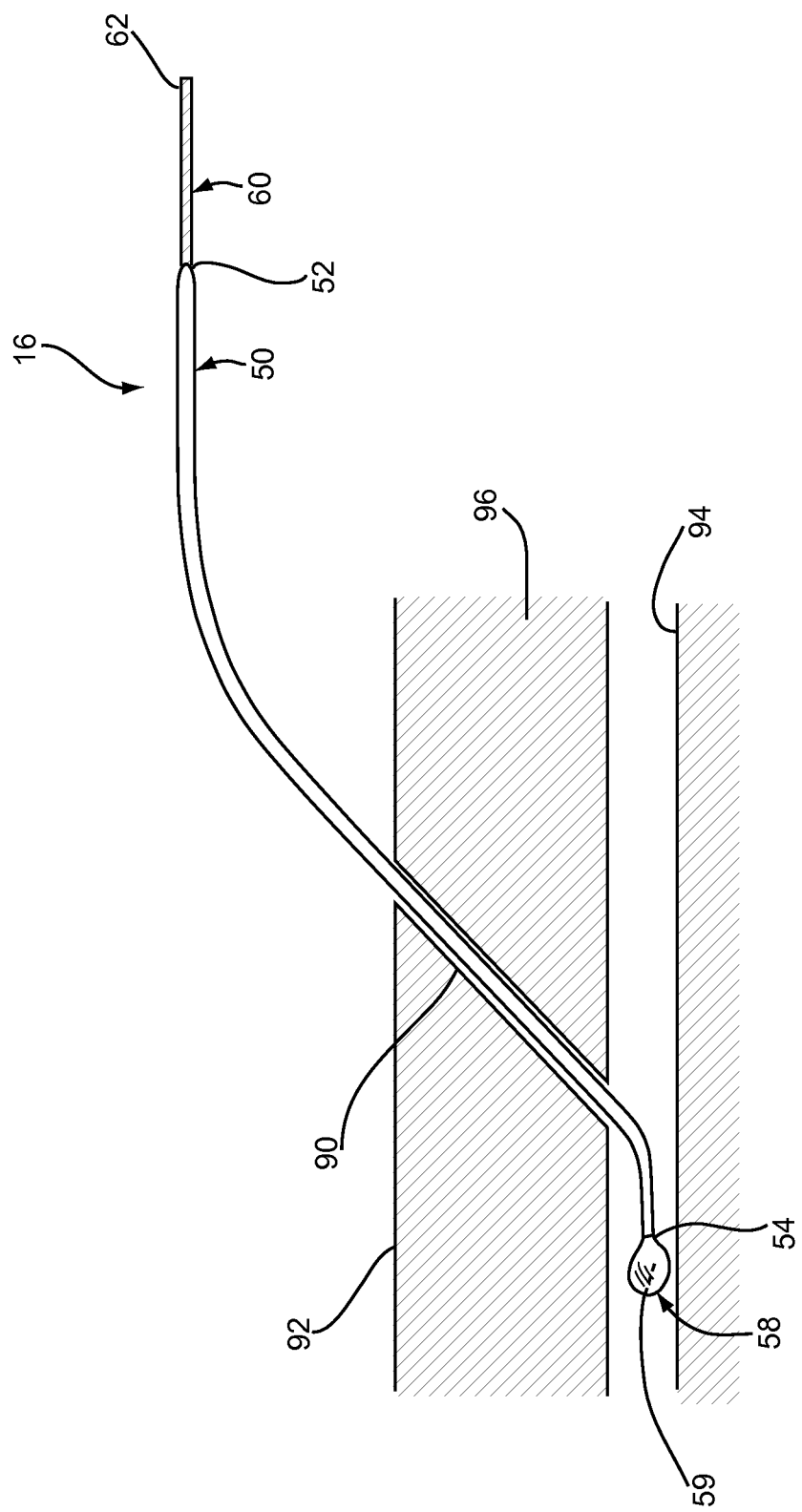
Figure 3C:
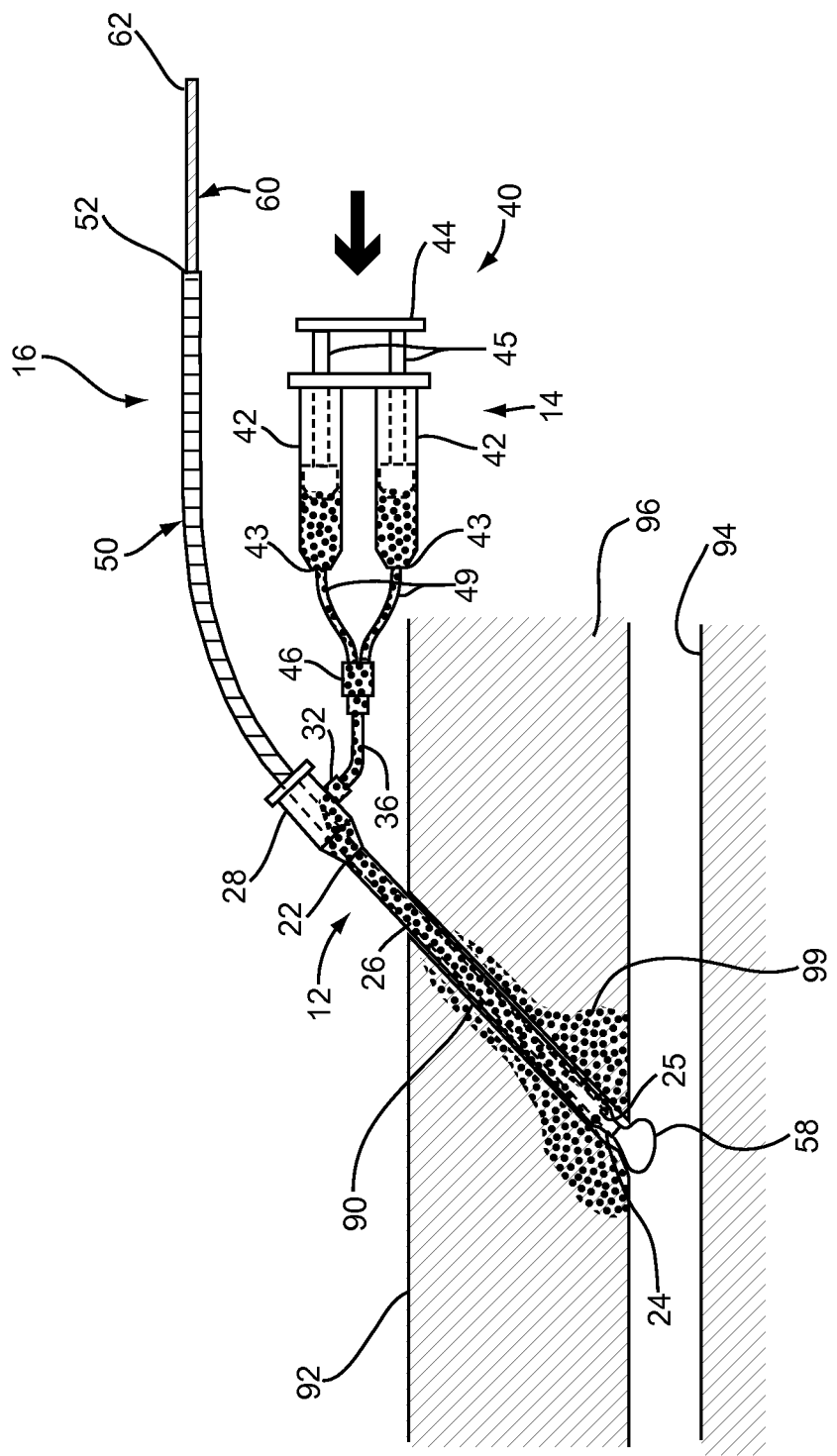

Initially, as shown in FIGS. 3A-3C, the puncture 90 may be created and sealing compound 99 may be delivered into the puncture 90. Turning to FIG. 2A, to create the puncture 90, a hollow needle 15 may be inserted through the patient's skin 92 and intervening tissue 96 into the vessel 94. The occlusion member 16, e.g., with the wire member 50 loaded with the piston 60 sealing fluid therein, may be inserted into the puncture 90, e.g., through the needle 15 until the distal tip 66 is disposed within the vessel 94. Optionally, as shown, the retaining sheath 17 may cover the balloon 58 on the wire member 50 as the occlusion member 16 is advanced through the needle 15, thereby maintaining the balloon 58 in the contracted or collapsed condition.

Turning to FIG. 2B, once the balloon 58 is located within the vessel 94, the needle may be removed, and the balloon 58 may be expanded within the vessel 94. For example, the retaining sheath 17 may be retracted completely (or only partially) out of the puncture 90 to expose the balloon 58 within the vessel 84.

The balloon 58 may then be expanded within the vessel 94. For example, as shown in FIG. 2B, the piston 60 may be advanced distally relative to the wire member 50. As the piston 60 is advanced within the wire member 50, fluid within the lumen 56 may enter the interior 59 of the balloon 58, causing the balloon 58 to expand. As described above, the wire member 50 and/or piston 60 may include one or more elements that tactile and/or audio feedback to provide an indication that the piston 60 has been advanced to a position where the balloon 58 is fully expanded.

Turning to FIG. 3C, with the balloon 58 fully expanded, a delivery sheath, such as the delivery sheath 12 described above, may be advanced over the occlusion member 16 into the puncture 90, e.g., before or after the balloon 58 is expanded. For example, the proximal end 62 of the piston 60 may be backloaded into the distal end 24 of the delivery sheath 12, and then the delivery sheath 12 may be advanced over the piston 60 and wire member 50 until the distal end 24 enters the vessel 94. Because of the substantial uniformity in cross-section and size of the piston 60 and wire member 50, the delivery sheath 12 may pass easily over the occlusion member 16. Alternatively, the proximal end 52 of the wire member 50 may include a transition, e.g., a ramped proximal edge (not shown) to facilitate advancing the delivery sheath 12 over the wire member 50.

In one embodiment, the delivery sheath 12 may be advanced until the distal end 24 is disposed within the vessel 94. The balloon 58 may then be expanded (if not expanded before introducing the delivery sheath 12), and the occlusion member 16 may be partially retracted until the balloon 58 contacts the distal end 24 of the delivery sheath 12 (providing a first tactile feedback). The occlusion member 16 may be retracted by pulling on the proximal end 52 of the wire member 50 unless the piston 60 is locked relative to the wire member 50, whereupon the piston 60 may be pulled. Otherwise, the piston 60 may be retracted relative to the wire member 50, which may prematurely deflate the balloon 58 or even release the fluid within the lumen 56 of the wire member 50.

The occlusion member 16 may then be pulled further until the balloon 58 contacts the wall of the vessel 94 (providing a second tactile feedback), thereby partially in retracting the delivery sheath 12 back into the puncture 90, e.g., until the distal end 24 is disposed adjacent the vessel 94.

Alternatively, the occlusion member 16 may be retracted until the occlusion element 51 contacts the wall of the vessel 94 before the delivery sheath 12 is introduced. The delivery sheath 12 may then be advanced into the puncture 90 until the distal end 24 contacts the expanded balloon 58, thereby providing tactile feedback that the outlets 25 of the delivery sheath 12 are disposed within the puncture 90 proximal to the vessel 94.

With continued reference to FIG. 3C, a source of sealing compound 14, e.g., the dual syringe assembly 40 described above, may be prepared and connected to the side port 32 of the delivery sheath 12, e.g., via tubing 49, either before or after the delivery sheath 12 is advanced into the puncture 90. The sealing compound 99 may then be delivered through the secondary lumen 30 and the outlets 25 and into the puncture 90. The sealing compound 99 may flow radially outwardly to permeate at least partially into the tissue surrounding the puncture 90.

Optionally, the delivery sheath 12 may be retracted as the sealing compound 99 is delivered, e.g., to fill the puncture 90 along its length. Additional apparatus and methods for delivering the sealing compound 99 into the puncture 90 around the occlusion member 16 are disclosed in co-pending application Ser. Nos. 10/454,362 and 10/745,946, incorporated above, or in co-pending application Ser. No. 10/975,205, filed Oct. 27, 2004, the entire disclosure of which is expressly incorporated by reference herein.

Once a desired amount of the sealing compound 99 is delivered into the puncture 90, the occlusion member 16 may be maintained such that the balloon 58 continues to seal the puncture 90 from the vessel 94, e.g., for sufficient time for the sealing compound 99 to at least partially or completely cure. Thereafter (or immediately after filling the puncture 90), the delivery sheath 12 may be removed entirely from the puncture 90.

The balloon 58 may then be deflated and the occlusion member 16 may be removed from the vessel 94 and puncture 90. In one embodiment, the balloon 58 may be deflated by moving the piston 60 proximally relative to the wire member 50. This action may withdraw the fluid within the interior 59 of the balloon 58 back into the lumen 56 of the wire member 50, thereby substantially collapsing the balloon 58. With the balloon 58 collapsed, the occlusion member 16 may simply be pulled proximally out through the puncture 90.

If the piston 60 is locked relative to the wire member 50, the lock (not shown) may need to be disengaged. Alternatively, if the lock is not releasable, the piston 60 may be pulled with sufficient force to break the lock. Optionally, the piston 60 may be removed entirely from the wire member 50, thereby releasing the fluid within the lumen 56 of the wire member 50 and exposing the lumen 56 and interior 59 of the balloon 58 to the ambient pressure of the surroundings.

The wire member 50 may be withdrawn before or after removing the delivery sheath 12. If the delivery sheath 12 remains within the puncture 90 while the wire member 50 is removed, the balloon 58 may be forced to collapse as it enters the delivery sheath 12. If the piston has been removed or withdrawn proximally beyond the side port(s) 53 in the wire member 50, this action may force any residual fluid within the balloon 58 out of the balloon 58 and out the side port(s) 53 and/or proximal end 52 of the wire member 50.

Figure 4C:
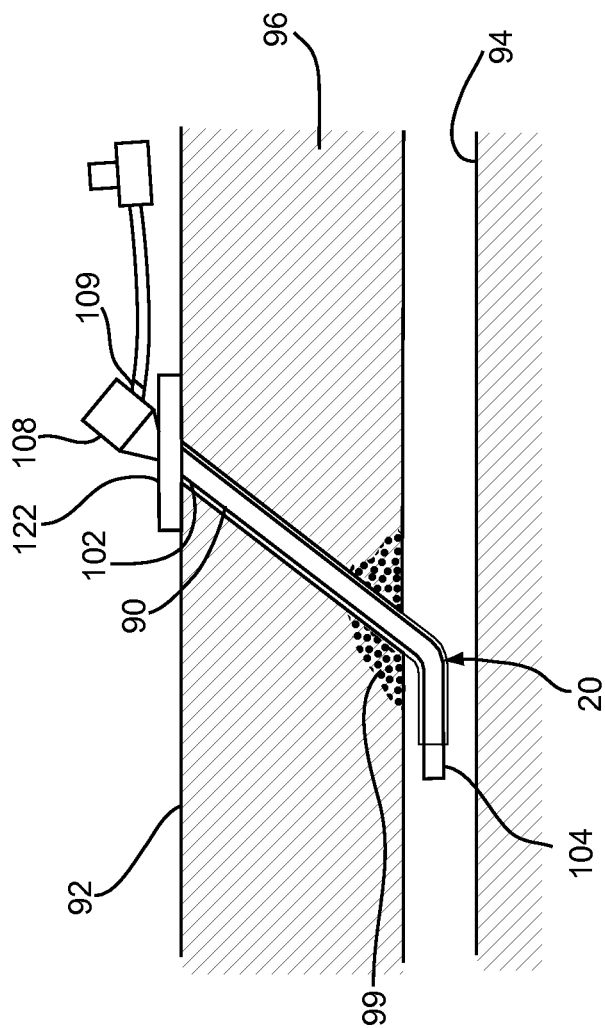

Optionally, turning now to FIGS. 4A-4C, an introducer sheath 18 and/or flexible sleeve 20, such as those described above and disclosed in the above-incorporated ACI-010 application, may be delivered into the puncture 90 and/or through the sealing compound 99. The sleeve 20 may prevent sealing compound 99 from separating and/or otherwise being released during introduction of the introducer sheath 18, as explained further below. Alternatively, the sleeve 20 may be omitted entirely.

As shown in FIG. 4A, the wire member 50 (or the entire occlusion member 16) may remain within the puncture 90 and vessel 94 after delivering the sealing compound 99. Optionally, the balloon 58 (not shown) may remain exposed and/or expanded, or the optional retaining sheath 17 (also not shown) may be advanced over the wire member 50 to cover and/or collapse the balloon 58. Alternatively, the wire member 50 may be removed from the puncture 90 and a separate guidewire (not shown), e.g., without balloon 58, may be advanced through the puncture 90 into the vessel 94 in place of the wire member 50.

Turning to FIG. 4B, the introducer sheath 18, dilator 19, and sleeve 20 may then be introduced into the puncture 90, e.g., over the wire member 50 (or the entire occlusion member 16). For example, the proximal end 52 of the wire member 50 and/or the proximal end 62 of the piston 60 may be backloaded into the introducer sheath 18 before the introducer sheath 18 is advanced into the puncture 90. Optionally, hub 122 of the sleeve 20 may be placed against or immediately above the patient's skin 92 overlying the puncture 90.

Turning to FIG. 4C, the introducer sheath 18 (and any of the dilator 19 and/or sleeve 20 carried therein) may then be advanced into the puncture 90, e.g., until the distal end 104 of the introducer sheath 18 is disposed within the vessel 94. As the introducer sheath 18 is advanced, the sleeve 20 may unfurl from the introducer sheath 18 and become exposed within the puncture 90, e.g., everting and surrounding the exterior of the introducer sheath 18. In the embodiment shown, the length of the sleeve 20 is shorter than the introducer sheath 18 such that the free end of the sleeve 20 is disposed proximal to the distal end of the introducer sheath 18 and may not extend into the vessel 94.

The dilator 19 and/or tubular member (not shown) may be withdrawn through the introducer sheath 18 from the puncture 90, e.g., together or successively, leaving the introducer sheath 18 and sleeve 20 within the puncture 90. The wire member 50 (or entire occlusion member 16) may also be removed along with, before, or after the dilator 19 and/or tubular member, e.g., after collapsing the balloon 58 (not shown). Alternatively, if the balloon 58 is still expanded, the wire member 50 may be removed, causing the introducer sheath 18 or dilator 19 to collapse the balloon 58 towards the collapsed state as it enters the lumen of the introducer sheath 18.

Once the distal end of the introducer sheath 18 is disposed within the vessel 94, one or more instruments (not shown) may be advanced through the introducer sheath 18 into the vessel 94, e.g., to perform one or more diagnostic and/or interventional procedures within the patient's body, as is known to those skilled in the art. The sleeve 20 generally does not interfere with the introduction of such instruments, since it is located only around the introducer sheath 18.

Optionally, if the sleeve 20 includes any weakened seams, the sleeve 20 may be removed from around the introducer sheath 18 to provide a conventional introducer sheath arrangement for the subsequent procedure. For example, the sleeve 20 may separate into two or more pieces, e.g., along one or more predetermined seams (not shown). Thus, conventional procedures may be used without need for extra attention to the sleeve 20.

Upon completing any such procedures, the instrument(s) may be removed from the vessel 94 through the introducer sheath 18. The introducer sheath 18 and sleeve 20 (if remaining around the introducer sheath 18) may then be removed from the vessel 94 and puncture 90, e.g., simultaneously or successively. The sealing compound 99 and/or tissue may recoil sufficiently to substantially fill the puncture 90, thereby allowing and/or encouraging hemostasis to occur between the vessel 94 and puncture 90. Optionally, external pressure may be applied to the patient's skin 92 during removal of the introducer sheath 18, e.g., to further enhance sealing of the puncture 90 until hemostasis occurs.

Turning to FIGS. 5A and 5B, another embodiment of an occlusion member 116 is shown that may be included in a system, e.g., instead of the occlusion member 16 described above. The occlusion member 16 generally includes an elongate wire member or other tubular body 150 carrying a balloon or other expandable member 158. Similar to the previous embodiment, the wire member 150 includes a proximal end 152, a distal end 154, and a lumen 156 extending at least partially between the proximal and distal ends 152, 154. The wire member 150 may have an outer diameter or other cross-section between about 0.008-0.038 inch, e.g., not more than about 0.040 inch.

The wire member 150 may be substantially flexible or semi-rigid, e.g., to allow the wire member 150 to curve, bend, or otherwise adapt to anatomy through which it is advanced, yet have sufficient column strength to accommodate advancing the distal end 154 by pushing on the proximal end 152. The wire member 150 may be formed from one or more wire coil(s) (not shown) wound into an elongate tubular shape, optionally, including applied to the wire coil(s) to create a substantially nonporous wall or may be formed from a solid-walled tube, similar to the previous embodiment.

The balloon 158 may be expandable from a collapsed state (such as that shown in FIG. 5B) to an enlarged state (such as that shown in FIG. 5A), e.g., by introducing fluid into an interior 159 of the balloon 158. The balloon 158 may be formed from a flexible, substantially inelastic material, e.g., to provide a substantially noncompliant or semi-compliant balloon 159 that expands to a predetermined size, or the balloon 158 may be formed from an elastic material, such that the size of the balloon 158 depends upon the pressure or volume of fluid delivered into the balloon 158.

As shown, the balloon 158 is disposed proximal to a distal tip 155 of the occlusion member 116, as described further below. For example, the balloon 158 may include a first end 158a attached to a distal end 154 of a wire member 150 and a second end 158b attached to the distal tip 155. The distal tip 155 may be a rounded, tapered, and/or substantially blunt member providing a substantially atraumatic tip, e.g., including a "J" tip (not shown), if desired to facilitate advancement.

As shown, the proximal end 152 of the wire member 150 is substantially closed, e.g., by providing a plug, sealant, glue, or other seal material in the proximal end 152. Alternatively, the proximal end 152 may be capped using a cap or other element (not shown). Thus, the lumen 156 may be substantially isolated from the region surrounding the wire member 150.

To communicate with the lumen 156, the wire member 150 may include one or more ports or other openings 153 located in an intermediate region of the wire member 150, e.g., adjacent the proximal end 152. The port(s) 153 may communicate directly with the lumen 156, e.g., allowing a fluid source (not shown) to communicate with the lumen 156 from the outside environment surrounding the wire member 150, as described further below.

The occlusion member 116 may also include a spring or biasing mechanism, such as spring wire 160 within the lumen 156 or otherwise coupled to the wire member 150. The spring wire 160 may be formed from an elastic or superelastic material, e.g., stainless steel or Nitinol, that may be sufficiently flexible to bend within the wire member 150, yet have sufficient column strength to bias the spring wire 160 to extend axially. The spring wire 160 may be a solid wire, e.g., having a round or flat cross-section. Optionally, one or more other biasing mechanisms (not shown) may be provided or the biasing mechanism may be omitted.

The spring wire 160 may be an elongate member including a proximal end 162 that is fixed relative to the wire member 150, and a distal end 164 that is fixed relative to the distal tip 155. For example, the proximal end 162 of the spring wire 160 may be attached to the proximal end 162 of the wire member 150, e.g., using an adhesive, sonic or other welding, embedding the proximal end 162 in the seal material, and the like. The distal end 164 of the spring wire 160 may be similarly attached to the distal tip 155 or alternatively to the distal end 158b of the balloon 158.

The relative lengths and fixation points of the wire member 150 and the spring wire 160 may place the spring wire 160 under slight tension inside the wire member 50, thereby biasing the distal tip 155 away from the distal end 154 of the wire member 150. This may place the balloon 158 under tension, thereby minimizing the cross-section of the balloon 158 in the collapsed state. This bias provided by the spring wire 160 may facilitate collapsing the balloon 158 after a procedure, e.g., to facilitate withdrawing the balloon 158 from a puncture 90 (not shown), as described further below.

Turning to FIG. 3A, when fluid is delivered into the interior 159 of the balloon 158, e.g., using the devices and/or methods described further below, the balloon 158 may shorten as it expands. Consequently, this may place the spring wire 160 under a compressive stress, foreshortening the distance between the proximal and distal ends 162, 164 of the spring wire 160. To reduce the resulting stress, the spring wire 160 may partially coil or otherwise contort inside the lumen 156 of the wire member 150. This may cause the wire member 150 to curve or otherwise twist to reduce the stress imposed by the spring wire 160 when the wire member 150 is free from outside forces or constraints (such as tissue surrounding a puncture).

When fluid 54 is evacuated from the interior of the balloon 158, the balloon returns towards the collapsed state of FIG.

5B. This may release the compressive force on the spring wire 160, whereupon the spring wire 160 may resiliently extend, i.e., move the distal end 164 distally away from the proximal end 162. This may bias the balloon 158 to extend distally, i.e., elongate, as it returns towards the collapsed state, thereby minimizing the profile of the balloon 158.

Figure 6:
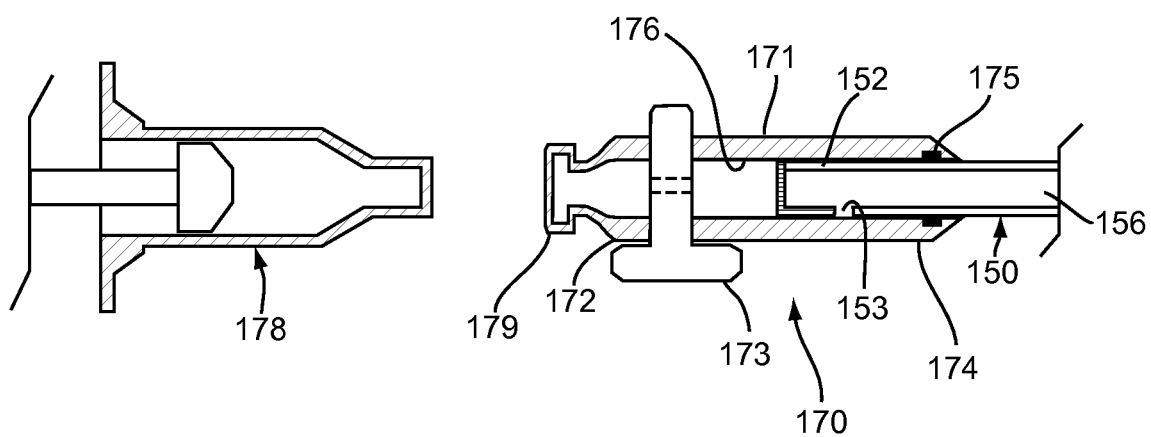
FIG. 6 is a cross-sectional side view of a fluid dispensing device and associated syringe for inflating and/or deflating the balloon of FIGS. 5A and 5B.

Turning to FIG. 6, an exemplary embodiment of a fluid loading device 170 is shown for delivering fluid into and out of the lumen 156 of the wire member 150, e.g., via the one or more side port(s) 153. The fluid may be used to selectively expand and/or collapse the balloon 58, similar to the embodiments described above. Generally, the fluid loading device 170 includes a housing 171 receivable on the proximal end 152 of the wire member 150, and a connector 179 for connecting to a source of vacuum or fluid, such as syringe 178, to the housing 171.

As shown, the housing 171 includes a proximal end 172 including the connector 179 thereon, a distal end 174, and a lumen or chamber 176 extending at least partially between the proximal and distal ends 172, 174. The distal end 174 is substantially open, having a size for receiving the proximal end 152 of the wire member 150 therein through the distal end 174 of the housing 171. The housing 171 may also include a shut-off mechanism 173 for selectively isolating or accessing the chamber 176 from the proximal end 172 of the housing 171.

The housing 171 has a sufficient length such that, when the housing 171 is advanced onto the proximal end 152 of the wire member 150, the distal end 174 of the housing 171 extends distally beyond the side port(s) 153 in the wire member 150. Thus, the side port(s) 153 in the wire member 150 may communicate with the chamber 176 around the proximal end 152 of the wire member 150. Optionally, the housing 171 may include a seal 175, such as a septum, o-ring, and the like, disposed within the distal end 174 of the housing. The seal 175 may be able to slide along the exterior of the wire member 150, yet create a substantially fluid-tight seal between the exterior of the wire member 150 and the distal end 174 of the housing 171.

The shut-off mechanism 173 may include a manual stopcock that may be rotated to allow a passageway therein to communicate between the proximal end 172 and the chamber 176 or isolate the chamber 176 from the proximal end 172 depending on its orientation (shown as open in FIG. 6). Alternatively, a valve or other manual or actuated shut-off mechanism (not shown) may be provided instead of the stopcock. The connector 179 may be a male or female Luer lock connector, or other connector for removably engaging with the syringe 178. Alternatively, the connector 179 and shut-off mechanism 173 may be replaced by a penetrable seal (not shown), e.g., which may be penetrated by a needle (also not shown) on the syringe 178.

Optionally, a locking mechanism (not shown) may be provided for securing the housing 171 to the proximal end 152 of the wire member 150. For example, a clamp or other device may be provided that may be tightened around the distal end 174 of the housing 171. Alternatively, the housing 171 may be sufficiently secured over the wire member 150 by friction or an interference fit.

Still referring to FIG. 6, during use, the housing 171 may be advanced onto the wire member 150, and a syringe 178 may be connected to the connector 179. With the shut-off mechanism 173 open, the syringe 178 may be drawn to evacuate substantially the air out of the lumen 156 of the wire member 150 and/or out of the interior 159 of the balloon 158. Fluid, e.g., saline or water, may then be delivered into chamber 176, and consequently into the lumen 156 and the interior 159 of the balloon 158 to expand the balloon 158. The shut-off mechanism 173 may be closed, and the syringe 178 may be disconnected, leaving the housing 171 on the proximal end 152 of the wire member 150.

When it is desired to collapse the balloon 158, the shut-off mechanism 173 may be opened, thereby allowing the fluid within the lumen 156 and the interior 159 of the balloon 158 to escape, e.g., to equalize the pressure within the balloon 158 to the surrounding ambient pressure. Alternatively, a syringe 178 or other source of vacuum may be connected to the connector 179, and the fluid may be evacuated actively from within the balloon 178 to collapse the balloon 178.

During a procedure, such as the sealing procedure described above, the occlusion member 116 may be advanced into a puncture (not shown), e.g., by introducing the distal end 154 of the wire member 150 into the puncture with the balloon 158 collapsed until the balloon 158 is disposed within a blood vessel (also not shown) accessed via the puncture. The occlusion member 116 may be advanced through a needle (not shown) used to create the puncture or through a delivery sheath (also not shown) already placed in the puncture. If a delivery sheath is not already in place, the delivery sheath may be advanced over the occlusion member 116, e.g., by backloading the proximal end 152 of the wire member 150 into the delivery sheath lumen.

The housing 171 may then be attached to the proximal end 152 of the wire member 150, which should be extending from the proximal end of the delivery sheath. Alternatively, the housing 171 may be attached to the proximal end 152 of the wire member 150 before the delivery sheath is introduced if the cross-section of the housing 171 is small enough to pass through the delivery sheath lumen.

The syringe 178 or other source of fluid may then be connected to the housing 171, e.g., after opening the shut-off mechanism 173, and fluid may be directed into the lumen 156 of the wire member 150 via the chamber 176 of the housing 171. Sufficient fluid may be introduced into the lumen 156 of the wire member 150 to substantially expand the balloon 158 to the enlarged state.

The expanded balloon 158 may then be used to seal the vessel from the puncture, e.g., by at least partially retracting the occlusion member 116 until the balloon 158 substantially engages the wall of the vessel. Sealing compound may then be delivered into the puncture via the delivery sheath, similar to the embodiments described above. Optionally, once sufficient sealing compound has been delivered into the puncture, the delivery sheath may be withdrawn from the puncture, and an introducer sheath (not shown) may be advanced over the occlusion member 116 into the puncture.

The balloon 158 may be collapsed and/or removed from the puncture, e.g., before or after placing the introducer sheath in the puncture. To collapse the balloon 158, the shut-off mechanism 173 may simply be opened, thereby allowing fluid to pass out of the interior 159 of the balloon 158, through the lumen 156, and possibly out of the proximal end 172 of the housing 171. Fluid may be affirmatively evacuated from within the balloon 158, or, with the shut-off mechanism 173 open, the occlusion member 116 may be withdraw, causing the balloon 158 to collapse as it pulled into the lumen of the introducer or delivery sheath.

While the above-described occlusion members have been described in connection with pre-sealing applications, it should be understood that the occlusion members described herein may be used during other procedures. For example, in one embodiment, an occlusion member, such as those described above, may be inserted into a puncture through tissue after completing a procedure that involves accessing a blood vessel or other body lumen via the puncture. Exemplary apparatus and methods for accessing a blood vessel or other body lumen, and/or for sealing the puncture after completing such a procedure are described in co-pending application Ser. No. 10/454,362, filed Jun. 4, 2003, incorporated by reference above, and Ser. No. 10/806,952, filed Mar. 22, 2004, the entire disclosure of which is expressly incorporated by reference herein.

While the invention is susceptible to various modifications, and alternative forms, specific examples thereof have been shown in the drawings and are herein described in detail. It should be understood, however, that the invention is not to be limited to the particular embodiments or methods disclosed, but to the contrary, the invention is to cover all modifications, equivalents and alternatives falling within the scope of the appended claims.

What is claimed:

1. An occlusion device for sealing a puncture through tissue, comprising:

an elongate tubular member comprising a proximal end, a distal end sized for insertion into a puncture, a lumen extending at least partially between the proximal and distal ends, and an expandable occlusion element carried on a distal region of the tubular member, the occlusion element having an interior communicating with a distal opening in the lumen, the tubular member having a uniform outside diameter extending between the proximal end and the distal region and including the proximal end; and an elongate piston member movable within the lumen of the tubular member for delivering fluid into, and drawing fluid out of, the interior of the occlusion element to thereby expand and collapse the occlusion element, the piston member having a proximal end extending from a proximal opening of the tubular member lumen.

2. The device of claim 1, the tubular member further comprising a port in a proximal region of the tubular member communicating with the lumen.

3. The device of claim 2, further comprising a fluid loading device connectable around the proximal region of the tubular member, such that the fluid loading device communicates with the port for delivering fluid from the fluid loading device into the lumen of the tubular member.

4. The device of claim 1, wherein the tubular member has an outer diameter of not more than about 0.040 inch.

5. The device of claim 1, wherein the tubular member comprises one or more wire coils defining a substantially nonporous wall of the tubular member.

6. The device of claim 1, wherein the tubular member comprises a solid-walled tubular body defining the lumen.

7. The device of claim 1, wherein at least one of the tubular member and the piston member comprises a locking mechanism for preventing distal movement of the piston member relative to the tubular member beyond a predetermined position.

8. The device of claim 7, wherein the locking mechanism comprises a ratchet mechanism that allows the piston member to be advanced distally relative to the tubular member to the predetermined position, but prevents the piston member from being directed proximally relative to the tubular member from the predetermined position.

9. The device of claim 7, wherein the locking mechanism comprises a tapered distal region on the tubular member and a correspondingly tapered shoulder on the distal end of the piston member.

10. The device of claim 1, wherein the piston member has a substantially uniform cross-section.

11. An occlusion device for sealing a puncture through tissue, comprising:

an elongate tubular member comprising a proximal end, a distal end sized for insertion into a puncture, a lumen extending at least partially between the proximal and distal ends, a port in a proximal region of the tubular member communicating with the lumen, and an expandable occlusion element carried on a distal region of the tubular member, the occlusion element having an interior communicating with a distal opening in the lumen; and a fluid loading device comprising a barrel connectable around the proximal region of the tubular member, such that the barrel surrounds all sides of the tubular member and the fluid loading device communicates with the port for delivering fluid from the fluid loading device into the lumen of the tubular member.

12. The device of claim 11, further comprising an elongate piston member movable within the lumen of the tubular member for delivering fluid into and drawing fluid out of the interior of the occlusion element to thereby expand and collapse the occlusion element, respectively, the piston member having a proximal end extending from a proximal opening of the tubular member lumen.

13. The device of claim 12, wherein at least one of the tubular member and the piston member comprises a locking mechanism for preventing distal movement of the piston member relative to the tubular member beyond a predetermined position.

14. The device of claim 12, wherein the piston member has a substantially uniform cross-section.

15. The device of claim 11, wherein the tubular member has an outer diameter of not more than about 0.040 inch.

16. The occlusion device of claim 11, further comprising a syringe coupled to the fluid loading device to deliver fluid into the lumen to allow expansion and collapse of the occlusion element.

17. The device of claim 16, further comprising an actuator on the proximal end movable between a proximal position and a distal position to deliver fluid into and draw fluid out of the interior of the occlusion element to thereby expand and collapse the occlusion element.

18. The device of claim 17, wherein the actuator comprises an elongate piston member movable within the lumen of the tubular member for delivering fluid into and drawing fluid out of the interior of the occlusion element.

19. The device of claim 16, wherein the tubular member has an outer diameter of not more than about 0.040 inch between the proximal end and the distal region.

20. The device of claim 16, wherein the tubular member has a substantially uniform outer cross-section such that a delivery sheath may pass easily over the occlusion device when the occlusion device is backloaded into the delivery sheath.

21. An occlusion device for sealing a puncture through tissue, comprising:

an elongate tubular member comprising a proximal end, a distal end sized for insertion into a puncture, a lumen extending at least partially between the proximal and distal ends, and a port in a proximal region of the tubular member communicating with the lumen;

an expandable occlusion element carried on a distal region of the tubular member, the occlusion element having an interior communicating with a distal opening in the lumen; an elongate piston member comprising a distal end movable within the lumen of the tubular member; and a fluid loading device connectable around the proximal region of the tubular member such that the fluid loading device communicates with the port for delivering fluid from the fluid loading device into the lumen of the tubular member, wherein the piston member is movable relative to the tubular member such that, when the piston member distal end is advanced distally beyond the port within the lumen, fluid loaded into the lumen is isolated from the fluid loading device, and the piston is movable for delivering fluid into, and drawing fluid out of, the interior of the occlusion element to thereby expand and collapse the occlusion element.

22. The device of claim 21, wherein the tubular member has a uniform outside diameter extending between the proximal end and the distal region.

23. The device of claim 22, wherein the tubular member is configured to accommodate at least one procedure device being advanced over the outside of the tubular member while the occlusion element is expanded.

24. The device of claim 21, wherein the fluid loading device comprises a barrel connectable around the proximal region of the tubular member such that the barrel surrounds the tubular member and the fluid loading device communicates with the port for delivering fluid from the fluid loading device into the lumen of the tubular member.

* * * * *